United States Patent
Anderson et al.

(10) Patent No.: US 11,253,723 B2
(45) Date of Patent: Feb. 22, 2022

(54) ANTI-MICROBIAL IRRADIATION FOR PERCUTANEOUS OSSEOINTEGRATED PROSTHESES (POPS)

(71) Applicant: THE GENERAL HOSPITAL CORPORATION, Boston, MA (US)

(72) Inventors: Richard Rox Anderson, Boston, MA (US); Lynn A. Drake, Braselton, GA (US); William A. Farinelli, Danvers, MA (US); Joshua Tam, Andover, MA (US)

(73) Assignee: THE GENERAL HOSPITAL CORPORATION, Boston, MA (US)

( * ) Notice: Subject to any disclaimer, the term of this patent is extended or adjusted under 35 U.S.C. 154(b) by 0 days.

(21) Appl. No.: 17/270,148

(22) PCT Filed: Aug. 20, 2019

(86) PCT No.: PCT/US2019/047162
§ 371 (c)(1),
(2) Date: Feb. 22, 2021

(87) PCT Pub. No.: WO2020/041245
PCT Pub. Date: Feb. 27, 2020

(65) Prior Publication Data
US 2021/0236847 A1    Aug. 5, 2021

Related U.S. Application Data

(60) Provisional application No. 62/765,297, filed on Aug. 20, 2018.

(51) Int. Cl.
*A61N 5/06* (2006.01)
*A61F 2/28* (2006.01)
(Continued)

(52) U.S. Cl.
CPC .......... *A61N 5/0624* (2013.01); *A61F 2/2814* (2013.01); *A61F 2/78* (2013.01);
(Continued)

(58) Field of Classification Search
CPC ............ A61F 2/2814; A61F 2002/7887; A61F 2002/0056; A61F 2002/0058;
(Continued)

(56) References Cited

U.S. PATENT DOCUMENTS

2003/0087217 A1*  5/2003  Coatoam ............... A61C 8/0075
                                                             433/173
2010/0317948 A1   12/2010  Dimauro et al.
(Continued)

FOREIGN PATENT DOCUMENTS

WO    2003/039390 A1    5/2003
WO    2007/127894 A1   11/2007
WO    2019/139644 A2    7/2019

OTHER PUBLICATIONS

Australian Examination Report for corresponding Australian Application Serial No. 2019326406, dated Apr. 29, 2021, pp. 1-6.
(Continued)

*Primary Examiner* — Christie L Bahena
(74) *Attorney, Agent, or Firm* — Tarolli, Sundheim, Covell & Tummino LLP (57) ABSTRACT

An osseointegrated fixture of a percutaneous osseointegrated prosthesis (POPs) anchors directly into a bone of a residual limb within an amputation stump. By anchoring directly into the bone, the POPs provides improved mobility, comfort, and function for an amputee, but an interface between an opening in the skin and the osseointegrated fixture, which allows the anchoring directly into the bone, is prone to infection by microbes. An anti-microbial device can be attached to and/or embedded within an extracorporeal
(Continued)

portion of the osseointegrated fixture to irradiate at least a portion on the interface with at least one wavelength of light selected for its antimicrobial effects.

15 Claims, 5 Drawing Sheets

(51) Int. Cl.
  *A61F 2/78* (2006.01)
  *A61L 2/08* (2006.01)
  *A61N 5/00* (2006.01)
(52) U.S. Cl.
  CPC ............... *A61L 2/084* (2013.01); *A61L 2/085* (2013.01); *A61F 2002/7887* (2013.01); *A61N 2005/005* (2013.01); *A61N 2005/0645* (2013.01); *A61N 2005/0658* (2013.01); *A61N 2005/0668* (2013.01)
(58) Field of Classification Search
  CPC ...... A61F 2002/0063; A61F 2002/0076; A61F 7/00; A61F 7/12; A61N 5/0624; A61N 2005/005
  See application file for complete search history.

(56) References Cited

U.S. PATENT DOCUMENTS

| | | | |
|---|---|---|---|
| 2013/0274896 A1* | 10/2013 | Wang | A61F 7/007 623/36 |
| 2014/0195002 A1 | 7/2014 | Bachus et al. | |
| 2014/0255869 A1* | 9/2014 | Kanno | A61C 8/0089 433/29 |
| 2015/0202452 A1 | 7/2015 | Skiera et al. | |
| 2016/0081822 A1 | 3/2016 | Zhe et al. | |
| 2017/0027720 A1 | 2/2017 | Pedtke et al. | |
| 2017/0157289 A1 | 6/2017 | Burns | |
| 2018/0200533 A1 | 7/2018 | Park et al. | |
| 2019/0053920 A1 | 2/2019 | Armitage | |

OTHER PUBLICATIONS

PCT International Search Report and Written Opinion for corresponding International Application Serial No. PCT/US2019/047162, dated Oct. 11, 2019, pp. 1-9.

Extended European Search Report for corresponding European Application Serial No. 19852639.4, dated Sep. 23, 2021, pp. 1-8.

* cited by examiner

ANTI-MICROBIAL IRRADIATION FOR PERCUTANEOUS OSSEOINTEGRATED PROSTHESES (POPS)

RELATED APPLICATIONS

This application claims the benefit of U.S. Provisional Application No. 62/765,297, entitled "METHODS TO PROVIDE ANTI-MICROBIAL BLUE LIGHT EXPOSURE FOR PERCUTANEOUS OSSEOINTEGRATED PROSTHESES," filed Aug. 20, 2018. The entirety of this application is hereby incorporated by reference for all purposes.

TECHNICAL FIELD

The present disclosure relates generally to percutaneous osseointegrated prostheses (POPs) and, more particularly, to using anti-microbial irradiation in connection with POPs to prevent microbial infection of an interface between an opening in the skin and an osseointegrated fixture.

BACKGROUND

Most commercially available prosthetics employ a conventional cup-shaped socket, which is fastened to the surface of an amputee's residual limb. However, the conventional cup-shaped sockets are associated with lack of mobility, poor function, and discomfort for amputees using the prosthetics. One way to address these problems is by utilizing percutaneous osseointegrated prostheses (POPs), in which an osseointegrated fixture is anchored directly into the bone and connected to a prosthetic. By directly anchoring into the bone, the osseointegrated fixture removes a layer of intervening soft tissue that sits between the bone and the prosthetic, thereby improving the mobility, function, and comfort for amputees using the prosthetic. However, the percutaneous nature of POPs necessitates an opening in the skin that is prone to infection by microbes. Such microbial infections can be prevented using drug or chemical-based anti-microbial agents, but with prolonged use, the microbes may develop a resistance to the drug or chemical-based anti-microbial agents.

SUMMARY

Despite numerous advantages, the risk of developing microbial infections limits the use of percutaneous osseointegrated prostheses (POPs). The present disclosure describes a way to prevent such microbial infection by applying anti-microbial irradiation to an interface between an opening in a patient's skin and an osseointegrated fixture of the POPs.

In one aspect, the present disclosure can include a system that delivers anti-microbial irradiation to at least a portion of a POPs to prevent microbial infection of an interface between an opening in the skin and the osseointegrated fixture. The system can include a POPs configured to create an interface between an osseointegrated fixture of the POPs and an amputation stump. The system can also include an anti-microbial device attachable to an extracorporeal portion of the osseointegrated fixture and configured to irradiate at least a portion of the interface with at least one wavelength of light.

In another aspect, the present disclosure can include an anti-microbial device attachable to an extracorporeal portion of an osseointegrated fixture. The anti-microbial device can be configured to irradiate at least a portion of an interface between an osseointegrated fixture of a POPs and an amputation stump with at least one wavelength of light, comprising one or more light sources configured to emit the at least one wavelength of light to irradiate the at least the portion of the interface.

In a further aspect, the present disclosure can include a POPs fixture. The POPs fixture (or osseointegrated fixture of the POPs) can have an extracorporeal portion having an exterior surface at least partially coated with at least one material having wave guiding properties. The wave guiding properties allow the coated area to guide at least one wavelength of light applied to one region of the POPs fixture along the POPs fixture and to emit the at least one wavelength of light from another region of the POPs fixture. The other region of the POPs fixture may be susceptible to microbial infection.

In yet another aspect, the present disclosure can include a method for delivering anti-microbial irradiation to prevent microbial infection of an interface between an opening in the skin and an osseointegrated fixture of a POPs. The method includes irradiating at least a portion of an interface between an osseointegrated fixture of the POPs and an amputation stump with at least one wavelength of light. The irradiating can be done using an anti-microbial device attachable to an extracorporeal portion of the osseointegrated fixture.

BRIEF DESCRIPTION OF THE DRAWINGS

The foregoing and other features of the present disclosure will become apparent to those skilled in the art to which the present disclosure relates upon reading the following description with reference to the accompanying drawings, in which.

DETAILED DESCRIPTION

Definitions

Unless defined otherwise, all technical and scientific terms used herein have the same meaning as is commonly understood by one of skill in the art to which the present disclosure pertains.

In the context of the present disclosure, the singular forms "a," "an" and "the" can also include the plural forms, unless the context clearly indicates otherwise.

The terms "comprises" and/or "comprising," as used herein, can specify the presence of stated features, steps, operations, elements, and/or components, but do not preclude the presence or addition of one or more other features, steps, operations, elements, components, and/or groups.

As used herein, the term "and/or" can include any and all combinations of one or more of the associated listed items.

Additionally, although the terms "first," "second," etc. may be used herein to describe various elements, these elements should not be limited by these terms. These terms are only used to distinguish one element from another. Thus, a "first" element discussed below could also be termed a "second" element without departing from the teachings of the present disclosure.

As used herein, the term "percutaneous osseointegrated prostheses" and/or "percutaneous osseointegrated prosthesis" (both referred to as POPs) can refer to one or more bone-anchored artificial body part. The POPs can include an osseointegrated fixture that anchor to the bone and link to the artificial body part.

As used herein, the term "osseointegration" can refer to the formation of a direct interface between an implanted osseointegrated fixture and bone without intervening soft tissue.

As used herein, the term "interface" can refer to the direct interface between the implanted osseointegrated fixture and bone, but may also include any soft tissue located in proximity to the opening in the skin and the osseointegrated fixture.

As used herein, the term "microbe" can refer to a pathogenic microorganism, including bacteria, fungi, protozoa, viruses, and the like. One example microbe can include a pathogenic bacteria.

As used herein, the term "microbial infection" can refer to the reaction of tissue to one or more microbes and/or toxins produced by the one or more microbes.

As used herein, the term "light" can refer to electromagnetic radiation that illuminates. The electromagnetic radiation can have wavelengths corresponding to ultraviolet radiation (e.g., between 10 nm and 400 nm), visible radiation (e.g., between 400 nm and 700 nm), and/or infrared radiation (e.g., between 700 nm and 1 mm).

As used herein, the term "waveguide" can refer to a structure that guides light with minimal loss of energy by restricting expansion to one dimension or two dimensions. In general, waveguide materials should have optical properties that are compatible with the wavelength(s) being used. In some instances, the waveguide materials should also have anti-microbial properties and/or at least not be easily colonized by microbes.

As used herein, the term "extracorporeal" can refer to something situated outside a patient's body.

As used herein, the terms "subject" and "patient" can be used interchangeably and refer to any amputee (individual with an amputated limb).

Overview

Percutaneous osseointegrated prostheses (POPs) include an osseointegrated fixture that anchors directly into bone of an amputated limb and connects to an artificial limb. Removing the soft tissue between the bone and the osseointegrated fixture results in improved mobility, comfort, and function, as well as a greater ease of use, for amputees using POPs compared to conventional cup-shaped sockets that are fastened to the surface of the amputated limb. However, the percutaneous nature of POPs requires an opening in the skin, which is prone to microbial infection. Traditional ways to avoid a microbial infection involve using drug or chemical-based anti-microbial agents, but microbes often develop a resistance to such drug or chemical-based anti-microbial agents. Certain wavelengths of light (e.g., wavelengths corresponding to blue light, red light, infrared light, near infrared light, or the like) are known to possess anti-microbial properties with a low risk of microbes developing resistance to the light after prolonged use. The present disclosure manipulates the anti-microbial properties of these certain wavelengths of light with an anti-microbial device that can be used in connection with POPs.

The anti-microbial device can be attached to and/or embedded within an extracorporeal portion of an osseointegrated fixture of a POPs to irradiate at least a portion of the interface between the opening in the skin and the osseointegrated fixture with the certain wavelength(s) of light. As one example, the anti-microbial device can be attached to an extracorporeal portion of the osseointegrated fixture to irradiate the areas between the osseointegrated fixture and the amputation stump. However, the light may be unable to irradiate certain regions of the interface, like skin folds and other complex geometries of the tissue. The present disclosure can overcome this limitation by embedding light source(s) of the anti-microbial device directly into the osseointegrated fixture and/or coating the osseointegrated fixture with one or more waveguide material(s) of the anti-microbial device.

Systems

Figure 1:
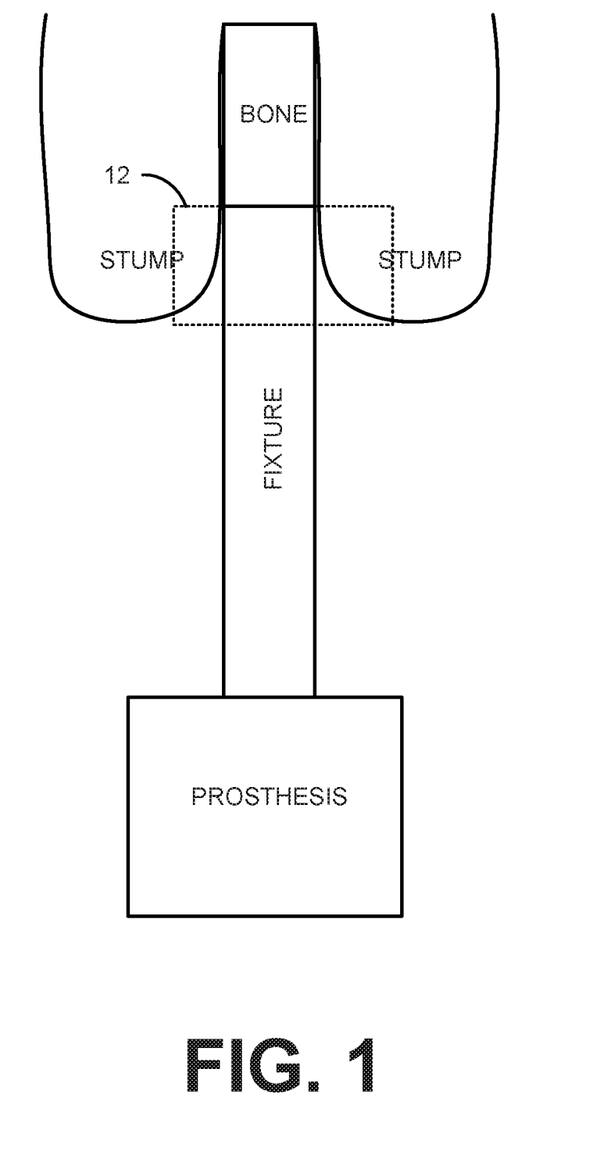
FIG. 1 is a diagram illustrating a percutaneous osseointegrated prostheses (POPs) emphasizing an area at high risk for infection.

As shown in FIG. 1, a percutaneous osseointegrated prostheses (POPs) includes an osseointegrated fixture (FIXTURE) that links bone within a residual limb (BONE), which is within an amputation stump (STUMP), and an artificial limb (PROSTHESIS). The osseointegrated fixture (FIXTURE) anchors directly into the bone within the residual limb (BONE), resulting in improved mobility, comfort, and function for amputees, compared to conventional cup-shaped sockets that are fastened to the surface of a residual limb. One disadvantage of the osseointegrated fixture (FIXTURE) is its percutaneous nature, which necessitates an opening in the skin (within interface 12) that is prone to infection by microbes. The interface 12 is of particularly high risk of microbial infection. The present disclosure describes a way to prevent such microbial infection by applying anti-microbial irradiation to at least a portion of the interface 12. It should be noted that the interface 12 is merely exemplary and can include more or less of the area enclosed by the box in FIG. 1.

Certain wavelengths of light (e.g., wavelengths corresponding to blue light, red light, infrared light, near infrared light, or the like) are known to possess anti-microbial properties. Additionally, the microbes have a low risk of developing resistance to the light after prolonged use. Accordingly, an anti-microbial device can manipulate these anti-microbial properties of the light in connection with a POPs. The anti-microbial device can be attached to, coated on, and/or embedded within an extracorporeal portion of the osseointegrated fixture (FIXTURE) to irradiate at least a portion of the interface 12 with one or more wavelengths of light according to one or more timing parameters chosen based on the application. The osseointegrated fixture (FIXTURE) can be constructed of a biocompatible material, which must be is stable under high loading conditions depending on the use of the artificial limb (PROSTHESIS). As one example, the osseointegrated fixture (FIXTURE) can include one or more metals, one or more polymers, one or more silicone-based material, or the like.

Figure 2:
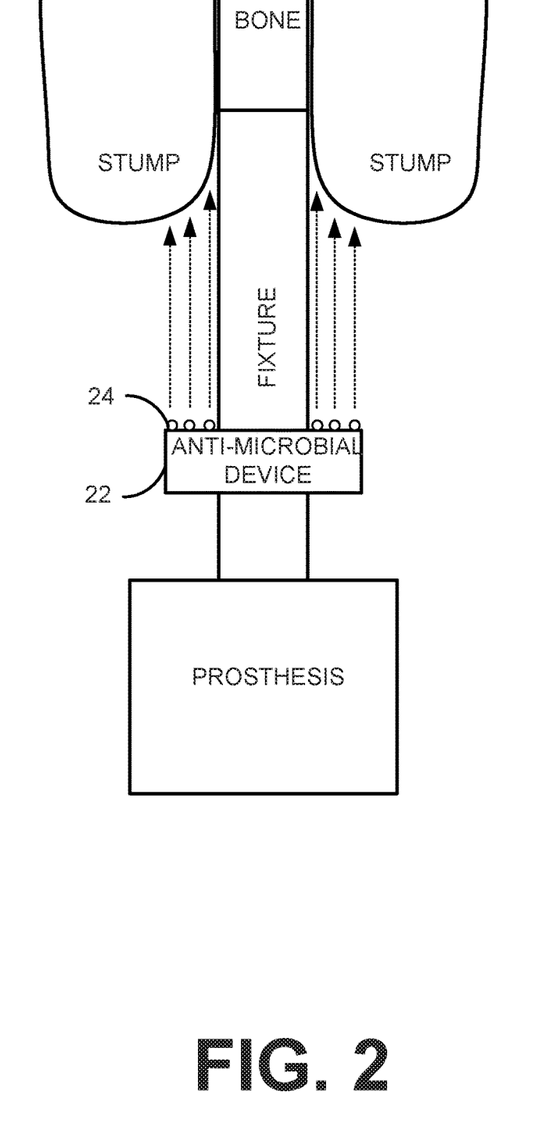
FIG. 2 is a diagram illustrating the POPs of FIG. 1 with a light-emitting attachment according to an aspect of the present disclosure.
Figure 3:
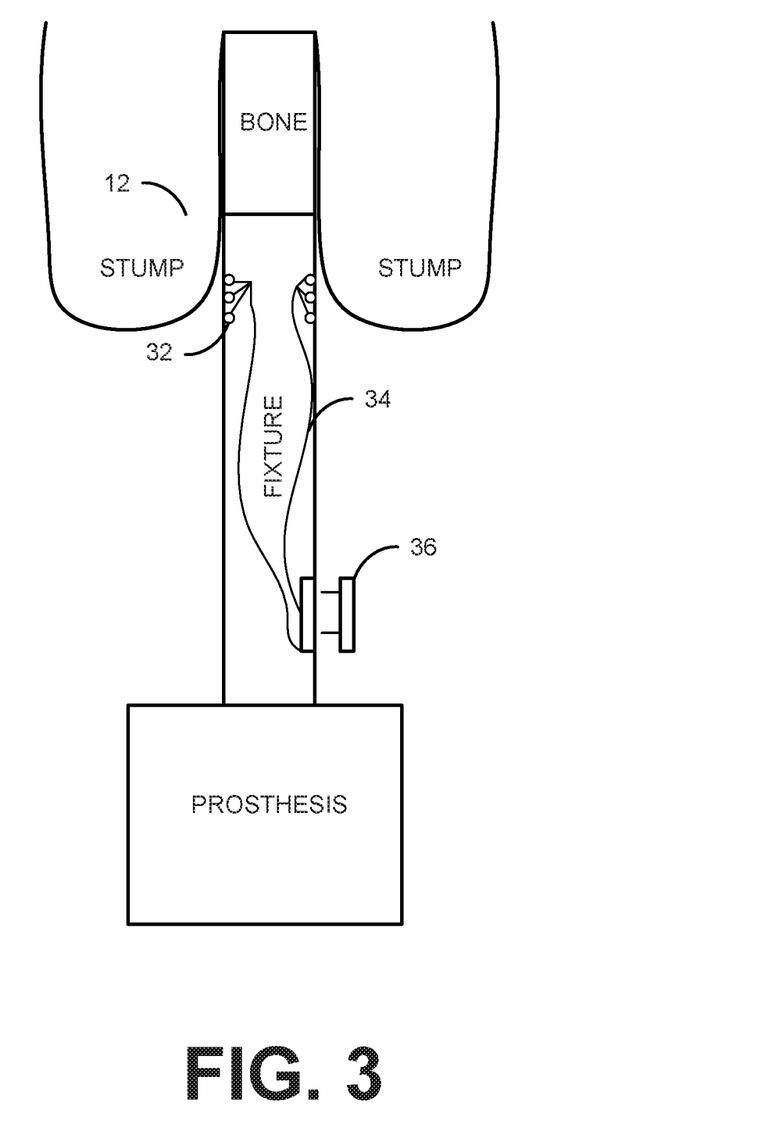
FIG. 3 is a diagram illustrating the POPs of FIG. 1 with light sources embedded in the osseointegrated fixture according to another aspect of the present disclosure.
Figure 4:
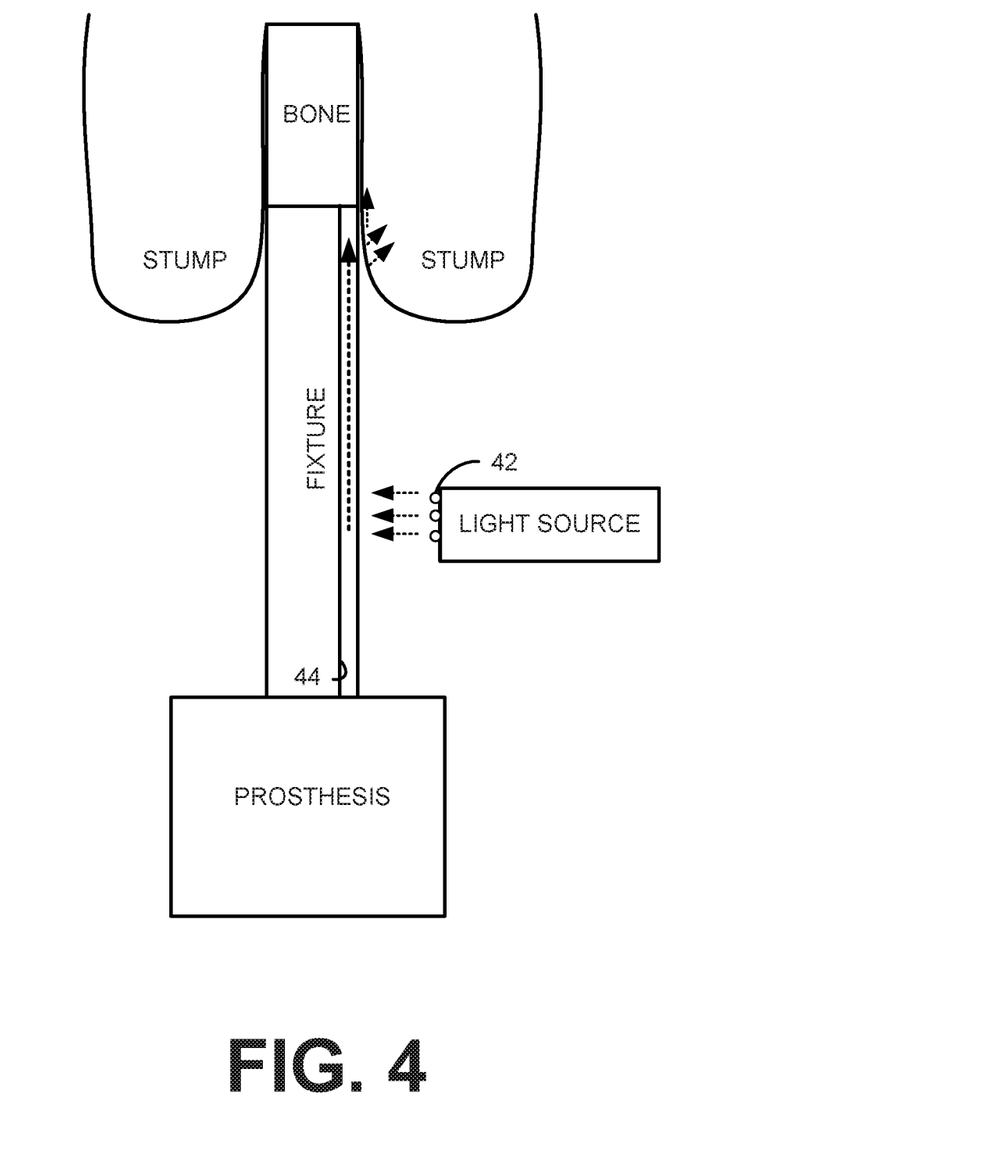
FIG. 4 is a diagram illustrating the POPs of FIG. 1 with a waveguide within the osseointegrated fixture.

As one example, shown in FIG. 2, the anti-microbial device 22 can be attached to the extracorporeal portion of the osseointegrated fixture (FIXTURE) to irradiate at least a portion of the areas between the osseointegrated fixture (FIXTURE) and the amputation stump (STUMP) (or the interface 12 of FIG. 1). In some instances, the light may be unable to irradiate certain regions of the interface 12, like skin folds and other complex geometries of tissue of the amputation stump (STUMP). FIGS. 3 and 4 show alternative designs that can irradiate these previously inaccessible regions. The designs of FIGS. 3 and 4 can be used separately or together. In the example of FIG. 3, light source(s) 32 of the anti-microbial device 22 are embedded directly into the osseointegrated fixture (FIXTURE). In the example of FIG. 3, the osseointegrated fixture (FIXTURE) can be coated with one or more waveguide material(s) to create one or more waveguides 44 of the anti-microbial device. The light emitted can be any type of light that shows significant anti-microbial effects. As an example, in each of FIGS. 2-4, the light delivered can have wavelengths corresponding to one or more of blue light, red light, infrared light, near infrared light, or the like.

As shown in FIG. 2, the anti-microbial device 22 can be attached to the extracorporeal portion of the osseointegrated fixture (FIXTURE). The attachment can be via a common screw-on or clip-on mechanism, such that, in some instances, the anti-microbial device 22 can be attached to and removed from the osseointegrated fixture (FIXTURE). For example, the anti-microbial device 22 can be removed from the osseointegrated fixture (FIXTURE) when not in active use. The anti-microbial device 22 can be in the form of a ring, a cap, or another form that enables light irradiation to at least a portion of the interface 12. The light delivered by the anti-microbial device 22 can be used as a stand-along treatment and/or in combination with other anti-microbial agents (e.g., anti-microbial agents, anti-microbial reagents, and the like). Moreover, if the amount of light needed to achieve satisfactory anti-microbial effects causes excessive heating (which may cause tissue damage and/or healing), a cooling system can be incorporated within the anti-microbial device 22 and/or external to the anti-microbial device 22 to reduce the temperature of the area(s) of the interface 12 being treated.

The anti-microbial device 22 can include one or more light sources 24. Six light sources 24 are shown in FIG. 2, but it will be understood that the anti-microbial device 22 can have any number of light sources greater than or equal to 1 limited by the geometry of the anti-microbial device. The light sources can be, for example, light emitting diodes (LEDs), laser diodes, or any other device configured to emit light of one or more certain wavelengths chosen for an application. Each light source 24 can emit one or more wavelengths and can be configured to emit the one or more wavelengths according to timing parameters. The one or more wavelengths can be chosen according to the type of microbe the light aims to eradicate and/or properties of the interface 12 (e.g., skin folds within the interface prone to microbial infection). In one example, a plurality of light sources 24 can emit the same wavelength. As another example, two or more of a plurality of light sources 24 can emit different wavelengths. In a further example, one or more of a plurality of light sources can be configured to emit different wavelengths depending on programming for the specific microbe being targeted. The timing parameters (e.g., length of irradiation with a certain wavelength of the one or more wavelengths, frequency of irradiation with the certain wavelength of the one or more wavelengths, periodic nature of irradiation with the certain wavelength of the one or more wavelengths, etc.) can vary based on the specific microbial species being eradicated.

As shown in FIG. 3, one or more light source(s) 32 can be embedded within and/or placed on the surface of the osseointegrated fixture (FIXTURE). The one or more light source(s) can be configured to emit light of one or more wavelengths outward from the osseointegrated fixture (FIXTURE) to irradiate areas of the interface 12 immediately adjacent to the osseointegrated fixture (FIXTURE). Six light sources 32 are shown in FIG. 3, but it will be understood any number of light sources can be embedded greater than or equal to 1 limited by the geometry of the osseointegrated fixture (FIXTURE). The one or more light source(s) 32 can be positioned within and/or placed on the surface of the osseointegrated fixture (FIXTURE) such that the external profile of the osseointegrated fixture (FIXTURE) is not compromised. In some instances, one or more filler material can be applied to the osseointegrated fixture (FIXTURE) to maintain a smooth surface topology. In some instances, the one or more filler materials can include optically clear polymer materials.

The wiring and/or connective elements 34 necessary to power the light sources 32 can also be embedded within the osseointegrated fixture (FIXTURE). However, at least a portion of the wiring and/or connective elements 34 can be outside the osseointegrated fixture (FIXTURE). A connection to an external power source 36 can be incorporated into the extracorporeal portion of the osseointegrated fixture (FIXTURE). For safety reasons, the external power source 36 can be a battery-powered power source. However, the external power source 36 may in some instances be a line power source. The external power source 36 can be disconnected when the one or more light source(s) 32 are not in use.

In FIG. 4, one or more material(s) with suitable wave guiding properties can be coated on the exterior surface of the osseointegrated fixture (FIXTURE) to create one or more waveguide(s). In addition to having the ability to guide at least one wavelength of light, the one or more material(s) can be biologically inert and stable in the environment of use (which may be warm and/or wet and may experience substantial mechanical loading). When light is applied by one or more light source(s) 42 to a region of the osseointegrated fixture (FIXTURE), the light can be emitted in another region of the osseointegrated fixture (FIXTURE) that would otherwise not be reachable. Three light sources 42 are shown in FIG. 4, but it will be understood any number of light sources can be used greater than or equal to 1. Additional coatings can be applied to the exterior surface of the osseointegrated fixture (FIXTURE) to achieve desired light conduction patterns (e.g., to allow light emission only in regions of the osseointegrated fixture (FIXTURE) and/or the interface 12 susceptible to microbial infection).

Generally, the one or more waveguide material(s) can be chosen with optical properties that are compatible with the wavelength(s) being used. In some instances, the one or more waveguide material(s) can also have anti-microbial properties and/or at least not be easily colonized by microbes. Examples of potential waveguide materials may include teflons, acrylates, epoxies, and/or silicones. Multiple waveguide materials may be coated on a surface of the osseointegrated fixture (FIXTURE), as one example, first with a waveguide material of a lower refractive index (n), then coating this first layer with a second layer with higher n (compared to the first layer). An alternate example involves optically polishing the surface of the osseointegrated fixture (FIXTURE) so that the surface reflects most/all of the light from the surface; in this scenario, only one layer of waveguide material would be needed.

Methods

Another aspect of the present disclosure can include a method 50 (FIG. 5) for delivering anti-microbial irradiation to prevent microbial infection of an interface (or area) between an opening in the skin and an osseointegrated fixture of a POPs. The method 50 can be performed using an anti-microbial device that can irradiate the areas between POPs and the residual limb (e.g., variations of the anti-microbial device 22 shown in FIGS. 2-4 and described above).

Figure 5:
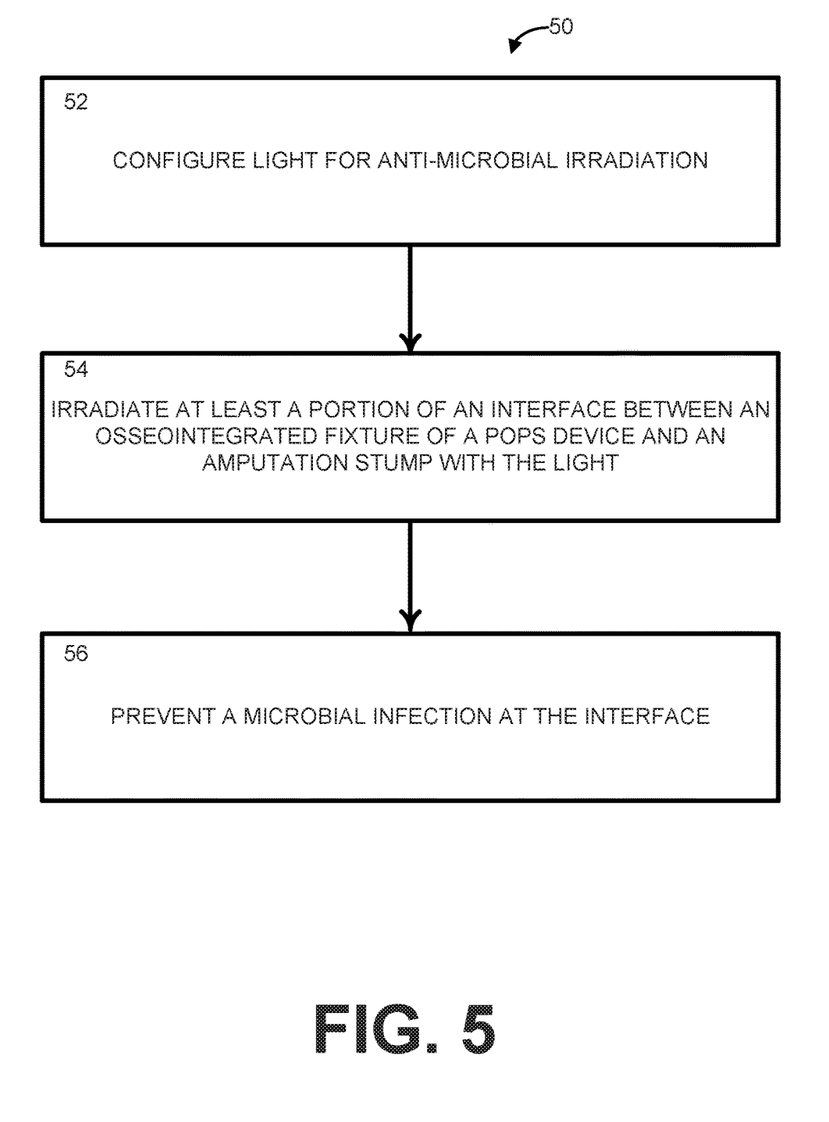
FIG. 5 is a process flow diagram illustrating a method for delivering anti-microbial irradiation to prevent microbial infection of an interface between an opening in the skin and an osseointegrated fixture of a POPs according to another aspect of the present disclosure.

The method 50 is illustrated as a process flow diagram with flowchart illustrations. For purposes of simplicity, the method 50 shown is and described as being executed serially; however, it is to be understood and appreciated that the present disclosure is not limited by the illustrated order as some steps could occur in different orders and/or concurrently with other steps shown and described herein. Moreover, not all illustrated aspects may be required to implement the method 50.

At 52, light can be configured for anti-microbial irradiation. The light can be configured with one or more wavelengths, timing parameters, and the like. For example, the light can be configured according to the type of microbe the light aims to eradicate and/or properties of the interface (e.g., skin folds within the interface prone to microbial infection). The timing parameters (e.g., length of irradiation with a certain wavelength of the one or more wavelengths, frequency of irradiation with the certain wavelength of the one or more wavelengths, periodic nature of irradiation with the certain wavelength of the one or more wavelengths, etc.) can vary based on the specific microbial species being eradicated.

At 54, at least a portion of the interface between the opening in the skin and the osseointegrated fixture of the POPs can be irradiated with the configured light. The light can be delivered by an anti-microbial device that can be attached to the osseointegrated fixture, coated onto the osseointegrated fixture, and/or integrated within the osseointegrated fixture. At 56, microbial infection can be prevented at the interface due at least in part to the light irradiation. Generally, the microbes do not tend to develop any resistance to the light be used in the method 50.

From the above description, those skilled in the art will perceive improvements, changes and modifications. Such improvements, changes, and modifications are within the skill of one in the art and are intended to be covered by the appended claims.

What is claimed is:

1. A system comprising:
    a percutaneous osseointegrated prosthesis (POPs) configured to create an interface between an osseointegrated fixture of the POPs and an amputation stump; and
    an anti-microbial device attachable to an extracorporeal portion of the osseointegrated fixture and configured to irradiate at least a portion of the interface with at least one wavelength of light,
    wherein at least a portion of an external surface of the extracorporeal portion of the osseointegrated fixture is coated with at least one material with waveguiding properties, and
    wherein the at least one material with waveguiding properties is coated by a different material to allow light emission only in regions of the extracorporeal portion of the osseointegrated fixture susceptible to microbial infection.

2. The system of claim 1, wherein the anti-microbial device comprises one or more light sources configured to emit the at least one wavelength of light to irradiate the at least the portion of the interface.

3. The system of claim 1, wherein the anti-microbial device is configured in a shape of a ring or a cap.

4. The system of claim 1, wherein the anti-microbial device is configured to attach to the extracorporeal portion of the osseointegrated fixture by a screw-on mechanism or a clip-on mechanism.

5. The system of claim 1, wherein the anti-microbial device is removable from the extracorporeal portion of the osseointegrated fixture.

6. The system of claim 1, wherein the anti-microbial device is embedded within the extracorporeal portion of the osseointegrated fixture to irradiate the at least the portion of the interface with at least one wavelength of light.

7. The system of claim 6, wherein at least a portion of the extracorporeal portion of the osseointegrated fixture is covered by a filler material.

8. The system of claim 7, wherein the filler material comprises an optically clear polymer.

9. A system comprising:
    a percutaneous osseointegrated prosthesis (POPs) configured to create an interface between an osseointegrated fixture of the POPs and an amputation stump;
    an anti-microbial device attachable to an extracorporeal portion of the osseointegrated fixture and configured to irradiate at least a portion of the interface with at least one wavelength of light; and
    a cooling system integrated within the anti-microbial device to reduce a temperature of the at least the portion of the interface irradiated with the at least one wavelength of light.

10. The system of claim 9, wherein the anti-microbial device is configured to attach to the extracorporeal portion of the osseointegrated fixture by a screw-on mechanism or a clip-on mechanism.

11. The system of claim 9, wherein the anti-microbial device is configured to be integrated within the osseointegrated fixture.

12. The system of claim 9, wherein the anti-microbial device is embedded within the extracorporeal portion of the osseointegrated fixture to irradiate the at least the portion of the interface with at least one wavelength of light.

13. A percutaneous osseointegrated prosthesis (POPs) fixture with an extracorporeal portion having an exterior surface at least partially coated with at least one material having wave guiding properties to guide at least one wavelength of light applied to one region of the POPs fixture along the POPs fixture and to emit the at least one wavelength of light from another region of the POPs fixture, wherein the other region of the POPs fixture is susceptible to microbial infection, wherein the at least one material having wave guiding properties is at least partially coated with another material to achieve a certain light conduction pattern along the POPs fixture.

14. The POPs fixture of claim 13, wherein the at least one material having wave guiding properties is biologically inert and stable in a percutaneous environment.

15. The POPs fixture of claim 13, wherein the at least one material having wave guiding properties is stable under conditions of mechanical loading.

* * * * *